(12) United States Patent
Huerta et al.

(10) Patent No.: US 8,431,226 B2
(45) Date of Patent: Apr. 30, 2013

(54) COATED MEDICAL DEVICE

(75) Inventors: Frank Huerta, San Carlos, CA (US);
Jennifer Elisseeff, Baltimore, MD (US);
Norman Marcus, Springfield, VA (US)

(73) Assignee: Biomet Manufacturing Corp., Warsaw, IN (US)

( * ) Notice: Subject to any disclaimer, the term of this patent is extended or adjusted under 35 U.S.C. 154(b) by 1023 days.

(21) Appl. No.: 11/909,833

(22) PCT Filed: Mar. 29, 2006

(86) PCT No.: PCT/US2006/011410
§ 371 (c)(1),
(2), (4) Date: Apr. 18, 2008

(87) PCT Pub. No.: WO2006/105161
PCT Pub. Date: Oct. 5, 2006

(65) Prior Publication Data
US 2009/0076606 A1    Mar. 19, 2009

Related U.S. Application Data

(60) Provisional application No. 60/666,405, filed on Mar. 30, 2005.

(51) Int. Cl.
*A61L 27/20* (2006.01)
*B32B 7/04* (2006.01)
*B32B 15/08* (2006.01)
*B32B 27/06* (2006.01)

(52) U.S. Cl.
USPC ......... 428/420; 428/464; 428/532; 623/16.11

(58) Field of Classification Search ......................... None
See application file for complete search history.

(56) References Cited

U.S. PATENT DOCUMENTS

| | | | |
|---|---|---|---|
| 4,352,883 A | 10/1982 | Lin | |
| 4,479,271 A | 10/1984 | Bolesky et al. | |
| 4,550,448 A | 11/1985 | Kenna | |
| 5,030,233 A | 7/1991 | Ducheyne | |
| 5,180,392 A | 1/1993 | Skeie et al. | |
| 5,282,861 A | 2/1994 | Kaplan | |
| 5,344,654 A | 9/1994 | Rueger et al. | |
| 5,364,839 A * | 11/1994 | Gerhart et al. | 514/8.2 |
| 5,380,328 A * | 1/1995 | Morgan | 606/70 |
| 5,458,653 A | 10/1995 | Davidson | |
| 5,947,893 A | 9/1999 | Agrawal et al. | |
| 5,977,204 A | 11/1999 | Boyan et al. | |
| 5,984,964 A | 11/1999 | Roberts et al. | |
| 6,105,235 A | 8/2000 | Caldarise | |
| 6,117,165 A * | 9/2000 | Becker | 623/1.15 |
| 6,156,068 A | 12/2000 | Walter et al. | |
| 6,159,531 A | 12/2000 | Dang et al. | |
| 6,461,628 B1 * | 10/2002 | Blanchard et al. | 424/402 |
| 6,514,286 B1 | 2/2003 | Leatherbury et al. | |
| 6,540,780 B1 | 4/2003 | Zilla et al. | |
| 6,599,558 B1 | 7/2003 | Al-Lamee et al. | |
| 6,679,914 B1 * | 1/2004 | Gabbay | 623/14.12 |
| 6,692,679 B1 | 2/2004 | McNulty et al. | |
| 6,709,739 B1 | 3/2004 | Mullen et al. | |
| 6,726,725 B2 | 4/2004 | Hunter et al. | |
| 6,818,332 B1 | 11/2004 | Niedhart et al. | |
| 6,974,482 B2 | 12/2005 | Zhu | |
| 6,984,394 B2 | 1/2006 | Menz et al. | |
| 7,727,547 B2 * | 6/2010 | Fortune et al. | 424/445 |
| 2004/0142016 A1 * | 7/2004 | Luthra et al. | 424/423 |
| 2004/0170663 A1 * | 9/2004 | Wang et al. | 424/423 |
| 2005/0002893 A1 * | 1/2005 | Goldmann | 424/70.27 |
| 2006/0002974 A1 | 1/2006 | Pacetti et al. | |
| 2010/0151532 A1 * | 6/2010 | Suzuki et al. | 435/101 |

FOREIGN PATENT DOCUMENTS

| | | |
|---|---|---|
| JP | 2002-106356 A | 10/2003 |
| WO | WO 93/17669 | 9/1993 |
| WO | WO 94/25080 | 11/1994 |
| WO | WO 2004087227 A1 * | 10/2004 |

OTHER PUBLICATIONS

International Search Report based on International Application No. PCT/US2006/011410 (Oct. 9, 2007).

* cited by examiner

*Primary Examiner* — Ramsey Zacharia
(74) *Attorney, Agent, or Firm* — Harness, Dickey

(57) ABSTRACT

Biologic coatings on a surface of a prosthesis or implantable device.

26 Claims, No Drawings

COATED MEDICAL DEVICE

CROSS-REFERENCE TO RELATED APPLICATIONS

This application is a 371 U.S. National Stage Application of International Application No. PCT/US06/11410 filed Mar. 29, 2006 which claims the benefit of U.S. Provisional Application No. 60/666,405 filed Mar. 30, 2005.

BACKGROUND OF THE INVENTION

The invention relates to coated prostheses, such as those for bone, made of any of a variety of materials. The coating of interest enhances adhesion of materials to the prosthesis, including biocompatible and biological molecules, such as cartilage. Any of the known prosthetic devices can be modified to carry the biological adhesive of interest, which adhesive can be used to attach compounds or structures thereto and to serve as a medium for interaction with a biological surface, a cell, tissue and the like.

The adhesive of interest is a monofunctional, bifunctional or polyfunctional biologically compatible polymer that adsorbs, absorbs, adheres, attaches, binds and the like to a surface of a prosthesis or other implantable device or structure. The polymer can be made from biological polymers or polymers that are biocompatible.

The invention also relates to prostheses coated with a hydrogel that is bonded to the surface of the prostheses.

SUMMARY OF THE INVENTION

It is an object of the instant invention to provide a biologically compatible coating that comprises at least two coating layers for use on prostheses and medical devices.

It is another object of the instant invention to provide a prosthesis that will integrate with the biological milieu within which it is situated.

It is yet another object of the instant invention to provide a surface on a prosthesis that promotes growth of biological structures thereon.

Those and other objects have been achieved in the development of materials and methods for modifying prosthesis surfaces with a biologically compatible adhesive that binds to the prosthesis surface and exposes additional reactive sites for reaction with other compounds, cells and the like or for providing a conducive environment for attachment of cells, tissues and the like.

Those and other objects have been achieved in the use of biologically compatible hydrogels that bind to the adhesive on a surface of a prosthesis or other implantable device or structure.

Additional features and advantages of the present invention are described in, and will be apparent from, the following Detailed Description of the Invention.

DETAILED DESCRIPTION OF THE INVENTION

The instant invention relates to a prosthesis or medical device, which terms are used interchangeably herein, having thereon a coating comprising at least two layers, that enhances adhesion of compounds thereto.

The prosthesis or medical device can be, for example, a replacement joint, a replacement bone or bone part, can have a dental use, can be used to fill a tissue defect or void, suitable tissues being, for example, bone and cartilage, can be a structure for providing support, such as a rod or a pin, can be a fastener, such as a staple and so on, can be used as a soft tissue adjunct, such as a tissue substitute or replacement, such as a graft or stent and so on.

The device of interest, which essentially is a hard surface or core having thereon or thereover a soft coating or layer finds utility at junctures or attachments of a hard tissue surface and a soft tissue surface, such as the meeting of bone and cartilage; bone and tendon; bone and ligament; and cartilage and muscle. The invention also finds utility in other uses, such as in dental applications, for example, at the juncture of a tooth and the soft tissue in the socket, and in the jaw bone, and so on. In such circumstances, a coated device of interest can contain a second functionalized polymer layer or coating of interest superior and attached to the at least one coating, such as a hydrogel, attached to the first functionalized polymer layer attached to a device surface.

The prosthesis or medical device can be of any composition, such as metal, ceramic, resin, biologic, polymer, graphite, plastic, diamond, glass and the like, as well as composites and mixtures thereof. The prosthesis can contain one or more of such composing materials. For example, a prosthesis can be made primarily of metal with one surface made of, for example, polyethylene. See, for example, U.S. Pat. No. 5,977,204.

Plastics include polyurethanes and polythylenes, see, for example, U.S. Pat. Nos. 6,984,394; 6,974,482; and 6,692,679. Ceramics can be metal oxides, such as aluminum oxides and zirconium oxides, see, for example, U.S. Pat. Nos. 6,726,725 and 6,105,235.

The prosthesis also can be one that is degradable, such as that taught in U.S. Pat. No. 5,180,392 for joining hollow parts of organs and tissues. See also U.S. Pat. No. 5,984,964. Attention also is directed to U.S. Pat. No. 6,540,780 which teaches a vascular prosthesis made from an elastomeric polymer.

The prosthesis can be a combination of a biodegradable and a non-biodegradable or a minimally biodegradable material.

As taught in U.S. Pat. No. 5,344,654, metal prostheses commonly are manufactured from stainless steel, titanium, molybdenum, cobalt, chromium, zirconium, tantalum, alloys thereof or oxides thereof. The oxides typically have a thin metal oxide surface coating.

A polymer of interest can react and adhere directly to the surface of the prosthesis or device of interest. Alternatively, a prosthesis or device of interest can be treated to have a reactive surface or can have thereon a coating, layer and the like to which a polymer of interest reacts as taught herein.

A coating of interest is any layer on a prosthesis or implantable device. Thus, a biocompatible polymer of interest on a device is a coating. A coating of interest can have any thickness, from one that is molecular in dimension to one that is macroscopic and in the millimeter or centimeter range, or portion thereof, and so on. Thus, a hydrogel layer attached to a polymer of interest on a device is a coating. The second of the two layers or coatings of interest, that which is distal to the prosthesis or device preferably is a hydrogel. As used herein, a coating refers to any and all the layers on a device of interest. Thus, for example, a coating comprises a bifunctionalized polymer and the at least one coating thereon.

The exposed surfaces of the prostheses or implantable device can be reacted with a coating of interest or the surface may be treated to make the surface more reactive. For example, U.S. Pat. No. 6,818,332 teaches treating prostheses comprised of oxide compounds, such as aluminum oxide, with lye to form hydroxides at the surface. U.S. Pat. No. 6,599,558 teaches a method of derivatizing a surface containing oxide or hydroxide groups with an alkoxysilane. Alternatively, the metals can be doped to provide chemically reactive compounds therein. A surface can be etched chemically or physically.

To enhance surface area, the device can contain holes, pits, undulations, channels, trabeculae, voids and the like, can be scaffold and so on, see, for example, Frosch et al., Cell Tissues Organs 170(4)214, 2002. Also, a device of interest can have a communication means connecting one surface of the device to another surface of the device, such as the superior and inferior surfaces of a device, which aside of the communication means is solid in structure, such as a channel, a tube and so on. The communication means can be direct, that is a single means connects the two surfaces, or can be indirect, and the result of interconnected means, such as a trabeculae, a rete, a plexus and the like, such as that found, for example, a sponge. The communication means can be empty or filled, for example, with a liquid or fluid, or for example, with a polymer and coating of interest. Thus, a communication means can be filled with a hydrogel. Such communications means enable the movement of cells, nutrients and the like from one side of the prosthesis or device to another side of the device. Such communication means connects one tissue or organ site with a site remote therefrom, such as the marrow contents of a bone with the surface of a prosthesis attached thereto, wherein one side of the prosthesis is in contact with the central cavity of a bone, and thus, the marrow, and the other surface of the prosthesis simulates the surface of the bone, wherein the marrow contents have access to the distal surface of the prosthesis via the communication means.

U.S. Pat. Nos. 6,156,068 and 6,514,286 teach a biocompatible film that can be used to cover a medical device. The film does not bind to the device but is secured to the device by mechanical, heat or electrical means. See also U.S. Pat. No. 5,458,653.

U.S. Pat. No. 6,159,531 teaches a method of treating the surface of a medical device with a plasma to provide a reactive layer thereon. The plasma deposited layer can yield functional groups, such as, amines, carbonyls and hydroxyls, covalently bound to the surface of the device.

Hence, it is preferred that a prosthesis have enhanced surface area, which can be achieved by using a device that is not solid but contains spaces, voids, texture, pore, holes, retes, networks and the like.

The exposed surfaces of the prostheses for receiving the coating of interest can be smooth or textured. For example, U.S. Pat. No. 4,550,448 teaches a metallic bone prosthesis containing a porous surface comprising ball-shaped metallic particles bonded together and to the surface. U.S. Pat. No. 5,282,861 teaches a metal foam made by chemical vapor deposition using, for example, tantalum or niobium. U.S. Pat. No. 4,479,271 teaches a porous metal prosthesis comprised of a fiber mesh material. U.S. Pat. No. 5,030,233 teaches using a porous metallic fiber mesh to enhance bone ingrowth therein. U.S. Pat. No. 6,709,739 teaches closed cell metal composites. See also U.S. Pat. No. 5,947,893.

The first layer which is the first coating of interest is bifunctional or polyfunctional, generally, a biologically compatible polymer functionalized with two or more different reactive moieties to provide an adhesive, that can be directional with plural reactive groups. In some embodiments, the composition comprises at least 10 monomeric units, at least 100 monomeric units or at least 1000 or more units of monomer. The polymer comprises plural copies of the reactive moieties. When plural reactive moieties are present, the second and other moieties can react with different chemical structures on different target entities to provide the polymer with a predetermined orientation and directed, specific reaction with a target structure or entity, the first moiety reacting with the prosthesis.

In one embodiment, a monomeric unit of the biologically compatible polymer has plural copies of one type of reactive moiety.

The reactive moiety may be selected, for example, from methacrylates, ethacrylates, itaconates, acrylamides and aldehydes.

In another embodiment, a monomer is functionalized with two types of reactive moieties.

In another embodiment, a monomer is functionalized with more than two reactive moieties.

In a polymer, not all monomers need be functionalized with a reactive moiety.

When plural species of reactive moieties are present, the polymer can contain equimolar or varying molar ratios of each species of reactive moiety relative to the whole. Thus, when two species of reactive moiety are present, substantially equal molar amounts of each of the two different reactive moieties. When more than two reactive moieties are present, generally, the moieties comprise two classes of molecules that are reactive with two target entities, that is, the moieties, while chemically distinct, react with the prosthesis, although, the reaction may be with two different chemical structures on the prosthesis, and the other class of moieties would react with another structure, entity and the like, such as a tissue, filler, hydrogel, medical device and the like.

In another embodiment, a polymer of interest comprising at least three classes of reactive moieties, a first class is reactive with a prosthesis or implantable device and at least two other classes are reactive with at least two other target entities.

In a polymer, to ensure directionality, either the backbone bonds of the polymer are flexible to obtain rotation about the axis of the polymer or all of one type of moiety are present on the same side of the polymer, or the moieties are in the same orientation on the polymer.

One functional moiety is reactive with a surface of the prosthesis, whether the surface is used as is or is treated in some way to enhance reaction with the adhesive of interest. A second functional moiety, if present, can be reactive with a target entity, an organ, tissue or cell, or may be reactive with a non-naturally occurring structure or biologically compatible material, such as a hydrogel or another prosthesis, the goal being to bring into proximity two like or dissimilar entities. The reaction of the polymer and the target, such as a prosthesis, can be through any means that provides a level of adhesion, such as a covalent bond, a physical crosslinking, an ionic crosslinking or other molecular mechanism that affixes the polymer onto the surface of the prosthesis.

In certain embodiments, multiple polymers are reacted together to form a multi-layer polymer structure with exposed surfaces having none or one or more reactive moieties thereon.

In certain embodiments, the polymer backbone is one that is minimally or not biodegradable. Such a polymer can be retained at the prosthesis surface for an extended time.

Compositions of the present disclosure may further comprise a biologically active agent, such as a nutrient, a nutrient medium, naturally occurring or not, such as a hydrogel or an extracellular matrix, or components thereof, a pharmaceutically active agent, a differentiated cell, such as a blood cell, an osteocyte, a cell of the immune system or a chondrocyte, or an undifferentiated cell, such as a stem cell, such as a hematopoietic stem cell or a mesenchymal stem cell, contained within or attached to the polymer or other coating, such as a hydrogel.

The disclosure provides for functionalized biologically compatible polymers, such as hyaluronate, keratan sulfate, chondroitin sulfate and the like, which can serve as a means to attach a compound, tissue, organ, cell, device and the like to a surface of a prosthesis.

The term "biologically compatible polymer or hydrogel" refers to a polymer or hydrogel that is a naturally occurring or one that is not toxic to the host. Generally, the metabolites of the polymer or hydrogel of interest also are not toxic to the host. The polymer may be a homopolymer where all constituent monomers are the same, a heteropolymer containing two or more kinds of monomers, a block polymer, a block copolymer and so on. It is not necessary that any subject composition have a purity of 100% to be deemed biocompatible; indeed, it is only necessary that the subject composition be non-toxic to the host. Hence, a subject composition may comprise monomer, polymers, hydrogels or portions thereof comprising 99%, 98%, 97%, 96%, 95%, 90%, 85%, 80%, 75% or even less of biocompatible monomer, polymers, hydrogels or portions thereof, e.g., including monomers, polymers, hydrogels or portions thereof, and other materials and excipients described herein, and still be biocompatible.

To determine whether a polymer, hydrogel or other material is biocompatible, it may be necessary to conduct a toxicity analysis. Such assays are well known in the art. One example of such an assay may be performed with live carcinoma cells, such as GT3TKJ3 tumor cells, in the following manner: the sample is used neat or is degraded in 1M NaOH at 37° C. until complete degradation is observed. The solution is then neutralized with 1M HCl. About 200 pL of various concentrations of the degraded sample products are placed in wells of 96-well tissue culture plates and seeded with indicator cells, such as human gastric carcinoma cells, such as GT3TKE3 cells, at $10^4$/well density. The degraded sample products are incubated with the cells for 48 hours. The results of the assay may be plotted as % relative growth vs. concentration of degraded sample in the tissue culture well. In addition, polymers, polymer matrices, hydrogels and formulations of the present invention may also be evaluated by well-known in vivo tests, such as subcutaneous implantations in rats, to confirm that significant levels of irritation or inflammation at the subcutaneous implantation sites do not occur. Acceptable levels of toxicity are as known in the art.

The terms "active agent," "pharmaceutically active agent" and "biologically active agent" are used interchangeably herein to refer to a chemical or biological compound that induces a desired pharmacological or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc.

The term "biodegradable" is art-recognized and is intended to indicate that an entity degrades during use. In general, degradation attributable to biodegradability involves the degradation of a biodegradable polymer into oligomers or its component subunits, or digestion, e.g., by a biochemical process, of the polymer into smaller subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to a side chain or that connects a side chain to the polymer backbone. The side chain may be a or the functional moiety or reactive moiety, which terms are used herein interchangeably. For example, a therapeutic agent, biologically active agent, or other chemical moiety attached as a side chain to the polymer backbone may be released by biodegradation. In certain embodiments, one or the other or both general types of biodegradation may occur during use of a polymer of interest. As used herein, the term "biodegradation" encompasses both general types of biodegradation as the overall desired function of the functionalized polymer of interest wanes. The same would apply to a hydrogel, many of which comprise polymers.

The degradation rate of a biodegradable polymer or hydrogel often depends in part on a variety of factors, including the chemical identity of linkages; the molecular weight, crystallinity, biostability and degree of cross-linking of such hydrogel or polymer; the physical characteristics of the structure, such as the shape and size; the mode and location of administration; and so on. For example, the greater the molecular weight, the higher the degree of crystallinity, and/or the greater the biostability, the biodegradation of any biodegradable polymer or hydrogel is usually slower. The term "biodegradable" is intended to cover materials and processes also termed "bioerodible". Generally, the rate of degradation is a design choice based on the monomers used.

In certain embodiments, the biodegradation rate of such hydrogel or polymer may be characterized by the presence of enzymes, for example, a particular protease, lipase, saccharidase and so on. In such circumstances, the biodegradation rate may depend on not only the chemical identity and physical characteristics of the polymer or hydrogel, but also on the identity, use, presence and the like of any such enzyme.

"Electromagnetic radiation" as used in this specification includes, but is not limited to, radiation having the wavelength of $10^{-20}$ to 10 meters. Particular embodiments of electromagnetic radiation of the instant invention employ the electromagnetic radiation of: γ radiation (to $10^{-20}$ to $10^{-13}$ m), x-ray radiation ($10^{-11}$ to $10^{-9}$ m), ultraviolet light (10 nm to 400 nm), visible light (400 nm to 700 nm), infrared radiation (700 nm to 1 mm) and microwave radiation (1 mm to 30 cm).

The term "functionalized" refers to a modification of an existing molecular segment to generate or introduce a new reactive or more reactive group (e.g., acrylate group) that undergoes reaction with another functional group (e.g., a sulfhydryl group) to form, for example, a covalent bond. Functionalized can be used herein interchangeably with "reactive." Thus, carboxylic acid groups can be functionalized by reaction with an acyl halide, e.g., an acyl chloride, again using known procedures, to provide a new reactive functional group in the form of an anhydride. Some functional or reactive groups may facilitate or mediate polymerization of the monomers into a polymer while other functional groups will mediate binding to the prosthesis and other structures.

The term "hydrogel" is used to refer to water-swellable polymeric matrices that can absorb water to form elastic gels, wherein "matrices" are defined as three-dimensional networks of macromolecules held together by covalent or noncovalent crosslinks. On placement in an aqueous environment, dry hydrogels swell to the extent allowed by the degree of cross-linking and the amount of liquid available. The amount of water absorbed can be controlled by the macromolecule used.

A hydrogel can carry a biologically active agent or a pharmaceutically active agent therein. Procedures for making a hydrogel that entraps and carries an agent, such as a drug, nutrient or cell, are known in the art and described herein.

The term "polymer" is used to refer to molecules composed of repeating monomer units, including homopolymers, block copolymers, heteropolymers, random copolymers, graft copolymers and so on. Polymers also include linear polymers as well as branched polymers, with branched polymers including highly branched, dendritic and star polymers.

A "monomer" is the basic repeating unit in a polymer. A monomer may itself be a monomer or may be dimer or oligomer of at least two different monomers, and each dimer or oligomer is repeated in a polymer.

A "polymerizing initiator" refers to any substance that can initiate polymerization of monomers or macromers by, for example, free radical generation. The polymerizing initiator often is an oxidizing agent. Exemplary polymerizing initiators include those which are activated by exposure to, for example electromagnetic radiation or heat.

Certain monomeric subunits of the present invention may exist in particular geometric or stereoisomeric forms. In addition, polymers and other compositions of the present invention also may be optically active. The present invention contemplates all such compounds, including cis and trans isomers, R and S enantiomers, diastereomers, d and l isomers, racemic mixtures thereof, and other mixtures thereof, as falling within the scope of the invention. Additional asymmetric carbon atoms may be present in a substituent, such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as an amino or an acidic functional group, such as carboxyl, diastereomeric salts are formed with an appropriate optically active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with the permitted valency of the substituted atom and the substituent, and that the substitution results in a stable compound, e.g., which does not spontaneously undergo transformation, such as by rearrangement, cyclization, elimination or other reaction.

The term "substituted" is also contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described hereinabove. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

In some embodiments, the disclosure is directed to a composition comprising at least one monomeric unit of a saccharide, such as hyaluronic acid, heparin sulfate, keratan sulfate and the like, functionalized by one or more reactive moieties. Those polysaccharides are natural components of extracellular matrices of cells and tissues. However, in general, any biologically compatible polymer can be used as the polymer, which polymer carries a functional group. Other suitable polymers include those which are naturally occurring, such as a GAG, mucopolysaccharide, collagen or proteoglycan component, such as glucosamines, dermatans, keratans, heparans, hyalurunan, aggrecan and the like. The biological polymer can be a polysaccharide, polypeptide, polynucleotide, lipid and so on, and combinations thereof.

Synthetic polymers that are biocompatible also can be used in the practice of the instant invention. Examples of such synthetic, biocompatible polymers are polyethylene glycol (PEG), polyvinyl alcohol (PVA) and block copolymers, such as the Pluronic compounds.

Suitable other polymers include biocompatible monomers with recurring units found in poly(phosphoesters), poly(lactides), poly(glycolides), poly(caprolactones), poly(anhydrides), poly(amides), poly(urethanes), poly(esteramides), poly(orthoesters), poly(dioxanones), poly(acetals), poly(ketals), poly(carbonates), poly(orthocarbonates), poly(phosphazenes), poly(hydroxybutyrates), poly(hydroxyl valerates), poly(alkylene oxalates), poly(alkylene succinates), poly (malic acids), poly(amino acids), poly(vinylpyrrolidone), poly(ethylene glycol), poly(hydroxycellulose), chitin, chitosan, and copolymers, terpolymers or combinations or mixtures of the above materials.

Other suitable synthetic polymers include polymers containing amine groups, such as chemically synthesized polypeptides. Such polypeptides may include polynucleophilic polypeptides that have been synthesized to incorporate amino acids containing primary amino groups for example, lysine and/or amino acids containing thiol groups (such as cysteine). Further suitable synthetic polymers include poly (amino)acids.

A polymer to be functionalized, or monomers thereof, can be obtained from commercial sources, extracted from natural sources using known methods or synthesized from monomers or oligomers, either made or purified as known in the art, or purchased, using methods known in the art.

A reactive moiety to functionalize a compound includes any moiety that is capable of reacting readily on exposure to a suitable chemical or chemical site on a target entity. A reactive moiety may include alkenyl moieties such as acrylates, methacrylates, dimethacrylates, oligoacrylates, oligomethacrylates, ethacrylates, itaconates or acrylamides. Further reactive moieties include carboxylates and aldehydes. Other reactive moieties may include ethylenically unsaturated monomers including, for example, alkyl esters of acrylic or methacrylic acid such as methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, benzyl methacrylate, the hydroxyalkyl esters of the same acids such as 2-hydroxyethyl acrylate, 2-hydroxyethyl methacrylate, and 2-hydroxypropyl methacrylate, the nitrile and amides of the same acids such as acrylonitrile, methacrylonitrile, methacrylamide, vinyl acetate, vinyl propionate, vinylidene chloride, vinyl chloride, and vinyl aromatic compounds such as styrene, t-butyl styrene and vinyl toluene, dialkyl maleates, dialkyl itaconates, dialkyl methylene malonates, isoprene and butadiene. Suitable ethylenically unsaturated monomers containing carboxylic acid groups include acrylic monomers such as acrylic acid, methacrylic acid, ethacrylic acid, itaconic acid, maleic acid, fumaric acid, monoalkyl itaconate including monomethyl itaconate, monoethyl itaconate, and monobutyl itaconate, monoalkyl maleate including monomethyl maleate, monoethyl maleate, and monobutyl maleate, citraconic acid and styrene carboxylic acid. Suitable polyethylenically unsaturated monomers include butadiene, isoprene, allylmethacrylate, diacrylates of alkyl diols such as butanediol diacrylate and hexanediol diacrylate, divinyl benzene and the like.

In some embodiments, a monomeric unit of a biologically compatible polymer may be functionalized through one or more thio, carboxylic acid or alcohol moieties located on a monomer of the polymer.

The reactive moieties are attached to the monomer or polymer using known chemistries based on design choice.

Thus, in producing a functionalized saccharide, a solution comprising the saccharide and a first functional group reactant, such as an alkylene or an acrylate group reactant, are mixed. The solution is stirred, for example, for at least 10 days, at least 11 days or at least 15 days. Alternatively, the solution may be stirred or maintained for about 10 to about 15 days or about 14 to about 15 days. The solution may include a polar solvent, for example an aqueous solvent.

Numerous chemical options are available for modifying polymers that then may undergo a radical polymerization. For example, methacrylic anhydride, methacryloyl chloride and glycidyl methacrylate may be used to add methacrylate groups to one or more monomers of a polymer chain. Glycidyl methacrylate may be used, for example, for efficiency of reaction. Further, the modification reagents may be chosen to optimize for a lack of cytotoxic byproducts.

In some embodiments comprising plural functional groups, the number of each of the reactive moieties per polymeric unit may be at least one moiety per about 10 monomeric units, or at least about 2 moieties per about 10 monomeric units. Alternatively, the number of reactive moieties per polymeric unit may be at least one moiety per about 12 monomeric units, or per about 14 monomeric units. For example, there may be at least about one methacrylate group per 15 or more monomeric units. The number of moieties also can range from one per monomer, one per two monomers, one per three monomers, one per 4, 5, 6, 7, 8 or 9 monomers.

When two different sorts of reactive groups are present on a polymer, the ratio of one of the two reactive groups to the other can be 5:1, 9:2, 4:1, 7:2, 3:1, 5:2, 2:1, 3:2, 1:1, 2:3, 1:2, 2:5, 1:3, 2:7, 1:4, 2:9 or 1:5 along the full length of the polymer. Preferably, each of the functional groups is regularly distributed along the length of the polymer and in substantially equal molar amounts. However, the amount of any one reactive group type is optimized for reaction with the intended target entity and may result in amounts where the ratio of the two types of reactive moieties deviates from unity. For example, one group of reactive moieties may be concentrated on one end of the polymer, and the other group of reactive moieties may be situated at the other end, to serve as a tether. The ratios of more than two reactive groups, one to another can be configured by the artisan based on the intended use.

The polymer of the invention can also comprise additional biocompatible monomeric units so long as there is no interference with the desirable characteristics of the invention. Such additional monomeric units may offer even greater flexibility in designing the precise profile desired for, for example, targeted drug delivery, tissue engineering or the precise rate of biodegradability or biocompatibility desired.

In another embodiment, a method of producing a multiple layer polymer is provided. A suitable monomer or polymer is exposed to at least one polymerizing initiator and successive reactions are performed thereby producing a multi-layer polymer of interest.

A polymerization reaction of the present invention can be conducted by conventional methods such as mass polymerization, solution (or homogeneous) polymerization, suspension polymerization, emulsion polymerization, radiation polymerization (using x-ray, electron beam or the like) or the like.

Polymerizing initiators include electromechanical radiation. Initiation of polymerization may be accomplished by irradiation with light at a wavelength of between about 200 to about 700 nm, or above about 320 nm or higher, or even about 365 nm.

Examples of other initiators are organic solvent-soluble initiators such as benzoyl peroxide, azobisisobutyronitrile (AIBN), dibutyl and tertiary butyl peroxide and the like, water soluble initiators such as ammonium persulfate (APS), potassium persulfate, sodium persulfate, sodium thiosulfate and the like, redox-type initiators which are combinations of such initiators and tetramethylethylene, $Fe^{2+}$ salt, sodium hydrogen sulfite or like reducing agent.

Useful photoinitiators are those which can be used to initiate by free radical generation polymerization of monomers with minimal cytotoxicity. In some embodiments, the initiators may work in a short time frame, for example, minutes or seconds. Exemplary dyes for UV or visible light initiation include ethyl eosin 2,2-dimethoxy-2-phenyl acetophenone, 2-methoxy-2-phenylacetophenone, other acetophenone derivatives and camphorquinone. In all cases, crosslinking and polymerization are initiated among macromers by a light-activated free-radical polymerization initiator such as 2,2-dimethoxy-2-phenylacetophenone or a combination of ethyl eosin and triethanol amine, for example.

Other photooxidizable and photoreducible dyes that may be used to initiate polymerization include acridine dyes, for example, acriblarine; thiazine dyes, for example, thionine; xanthine dyes, for example, rose bengal; and phenazine dyes, for example, methylene blue. These may be used with cocatalysts such as amines, for example, triethanolamine; sulphur compounds; heterocycles, for example, imidazole; enolates; organometallics; and other compounds, such as N-phenyl glycine. Other initiators include camphorquinones and acetophenone derivatives.

Thermal polymerization initiator systems may also be used. Such systems that are unstable at 37° C. and would initiate free radical polymerization at physiological temperatures include, for example, potassium persulfate, with or without tetramethyl ethylenediamine; benzoylperoxide, with or without triethanolamine; and ammonium persulfate with sodium bisulfite.

In one aspect of this invention, a composition comprising a polymer of interest, a multilayer polymer of interest, a hydrogel of interest or an entity attached to a polymer of interest may contain one or more biologically active agents. The biologically active agent may vary widely with the intended purpose for the composition. The term active is art-recognized and refers to any chemical moiety that is a biologically, physiologically, or pharmacologically active substance that acts locally or systemically in a subject. Examples of biologically active agents, that may be referred to as "drugs", are described in well-known literature references such as the Merck Index, the Physicians Desk Reference and The Pharmacological Basis of Therapeutics, and include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released by the subject composition, for example, into adjacent tissues or fluids on administration to a subject.

Further examples of biologically active agents include, without limitation, enzymes, receptor antagonists or agonists, hormones, growth factors, autogenous bone marrow, antibiotics, antimicrobial agents and antibodies. The term "biologically active agent" is also intended to encompass various cell types and genes that can be incorporated into the compositions of the invention.

In certain embodiments, the subject compositions comprise about 1% to about 75% or more by weight of the total composition, alternatively about 2.5%, 5%, 10%, 20%, 30%, 40%, 50%, 60%, 70% or more, of a biologically active agent.

Non-limiting examples of biologically active agents include following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials and pro-drugs.

Various forms of the biologically active agents may be used. These include, without limitation, such forms as uncharged molecules, molecular complexes, salts, ethers, esters, amides, and the like, which are biologically activated when implanted, injected or otherwise placed into a subject.

In certain embodiments, other pharmaceutically acceptable materials may be incorporated into subject compositions in addition to one or more biologically active agents. For example, plasticizers and stabilizing agents known in the art may be incorporated in compositions of the present invention. In certain embodiments, additives such as plasticizers and stabilizing agents are selected for their biocompatibility.

A composition of this invention may further contain one or more adjuvant substances, such as fillers, thickening agents or the like. In other embodiments, materials that serve as adjuvants may be associated with the composition. Such additional materials may affect the characteristics of the composition that results. For example, fillers, such as bovine serum albumin (BSA) or mouse serum albumin (MSA), may be associated with the polymer composition. In certain embodiments, the amount of filler may range from about 0.1 to about 50% or more by weight of the composition, or about percent. Incorporation of such fillers may affect the sustained release rate of any encapsulated substance. Other fillers known to those of skill in the art, such as carbohydrates, sugars, starches, saccharides, celluloses and polysaccharides, including and sucrose, may be used in certain embodiments in the present invention. An example of a thickener is hyaluronic acid.

Buffers, acids and bases may be incorporated in the compositions to adjust their pH. Agents to increase the diffusion distance of agents released from the composition may also be included.

The charge, lipophilicity or hydrophilicity of any subject composition may be modified by employing an additive. For example, surfactants may be used to enhance miscibility of poorly miscible liquids. Examples of suitable surfactants include dextran, polysorbates and sodium lauryl sulfate. In general, surfactants are used in low concentrations, generally less than about 5%.

Biologically active agents may be incorporated into the polymer or hydrogel by admixture. Alternatively, the agents may be incorporated into a hydrogel, a multi-layer polymer, or attached to a polymer of interest by binding the agents to the functional groups on the polymers. Such compositions may include linkages that can be easily biodegraded, for example as a result of enzymatic degradation, resulting in the release of the active agent into the target tissue, where it will exert its desired therapeutic effect.

A simple method for incorporating biologically active agents containing nucleophilic groups into the cross-linked polymer or hydrogel composition involves mixing the active agent with a polyelectrophilic component prior to addition of the polynucleophilic component. By varying the relative molar amounts of the different components of the reactive composition, it is possible to alter the net charge of the resulting cross-linked polymer or hydrogel composition, to prepare a matrix for the delivery of a charged compound such as a protein or ionizable drug. As such, the delivery of charged proteins or drugs, which would normally diffuse rapidly out of a neutral carrier matrix, can be controlled.

For example, if a molar excess of a component that is polynucleophilic is used, the resulting matrix may have a net positive charge and can be used to ionically bind and deliver negatively charged compounds. Examples of negatively charged compounds that can be delivered from these matrices include various drugs, cells, proteins and polysaccharides.

If a molar excess of a component that is polyelectrophilic is used, the resulting matrix has a net negative charge and can be used to ionically bind and deliver positively charged compounds. Examples of positively charged compounds that can be delivered from these matrices include various drugs, cells, proteins, and polysaccharides.

A polymer of the present invention can also be used to deliver various types of living cells or genes to a desired site of administration. The term "genes" as used herein is intended to encompass genetic material from natural sources, synthetic nucleic acids, DNA, antisense DNA, RNA and so on.

For example, mesenchymal stem cells can be delivered using the polymers or hydrogels of interest. Mesenchymal stem cells may not differentiated and therefore may differentiate to form various types of new cells due to the presence of an active agent or the effects (chemical, physical etc.) of the local tissue environment. Examples of mesenchymal stem cells include osteoblasts, chondrocytes and fibroblasts. For example, osteoblasts can be delivered to the site of a bone defect to produce new bone; chondrocytes can be delivered to the site of a cartilage defect to produce new cartilage; fibroblasts can be delivered to produce collagen wherever new connective tissue is needed; neurectodermal cells can be delivered to form new nerve tissue; epithelial cells can be delivered to form new epithelial tissues, such as liver, pancreas etc.

The cells or genes may be either allogeneic or xenogeneic in origin. For example, the compositions can be used to deliver cells or genes other species that have been genetically modified. In some embodiments, the compositions of the invention may not easily be degraded in vivo, cells and genes entrapped within the cross-linked polymer matrix compositions will be isolated from the patient's own cells and, as such, will not provoke an immune response in the patient.

To entrap the cells or genes within a polymer or hydrogel, the cells or genes may, for example be pre-mixed with a composition comprising functionalized polymer, and optionally a further biocompatible polymer. That may occur through a particular reaction or may occur during the making of a multiple layer polymer or hydrogel. Alternatively, the cells may be contained within a target entity attached to a polymer or hydrogel of interest.

The components of the reactive composition, such as monomers or oligomers can be infused to a desired site. The present invention may be prepared to include an appropriate vehicle for injection, implantation, infusion or direction. Once at the site, the functionalized biologically compatible polymer comprising at least two functional groups can be made to polymerize as taught herein. The polymer then will react with the surface of interest, such as a prosthesis. Thus, the polymer is anchored to the prosthesis surface. Alternatively, the polymer of interest may react with a prosthesis or implantable device without an initiator. An example is a polymer containing an aldehyde group, which can react with an amino group to form a covalent bond by a Schiff reaction. An entity reactive with the other reactive groups now exposed on the prosthesis, such as a chemically compatible hydrogel, then can be added to react with a polymer of interest, the result being the hydrogel now is anchored to the prosthesis.

Thus, in one embodiment, an adhesive of interest is allowed to attach to the surface of a prosthetic device, whether textured or not. The surface may be treated to enhance reactivity. The adhesive of interest can be preformed or polymerized on the prosthesis as taught herein. Thus, an adhesive carrying acrylate sites can react and adhere to a prosthesis carrying, for example, exposed amine groups. A prosthesis or relevant part thereof can be immersed in a reagent solution or such solution(s) can be applied as needed to the prosthesis surface, and polymerization initiated. Those activities can occur prior to implanting the prosthesis. Alternatively, all of the exposed surface of a prosthesis, such as an articulating surface and the like can be coated with an adhesive of interest, that is, the prosthesis can be immersed in a reagent solution.

Because the adhesive of interest is at least bifunctional, the result of adhering the adhesive to the prosthesis is to have a new reactive surface thereon contributed by the adhesive of interest. The new prosthesis surface can react with a biological structure in situ, such as a cell or fluid. Alternatively, the new prosthesis surface can react with a biocompatible structure, such as a hydrogel.

The location of the coating need not be restricted to the normally external surfaces of a prosthetic device, the entire external surface or portions thereof. For example, a bone prosthesis for use with a bone having a central cavity comprising marrow can contain a series of conduits communicating the marrow cavity with an external surface of the prosthesis. Such conduits can be direct, as in a manufactured means, such as a tube or other hollowed space connecting the surface with the marrow cavity, or may arise from the materials used to construct the prosthesis, which materials provide a conduit means. For example, the prosthesis or implantable device may comprise a mesh, a rete, a trabecula, a network or other pore-forming material such that a communication means between the marrow cavity and an external surface of the prosthesis exists.

Those "internal" exposed surfaces within the structure of the prosthesis also can be coated with an adhesive of interest to provide, for example, a surface conducive for cell adhesion. The application of the adhesive or hydrogel is as taught hereinabove.

In another embodiment, the adhesive of interest is used to attach or anchor a prosthesis or implant to a body site, such as a tissue, organ, bone and so on. Thus, an adhesive of interest having at least two sets of functional, reactive groups is provided, one set of functional groups being reactive with the prosthesis surface and the other set of functional groups being reactive with the body site.

In certain applications, a prosthesis can be coated with a hydrogel that binds to the prosthesis surface. The hydrogels of interest are derivatized to be reactive with functional groups found on the polymer on the prosthesis. The hydrogels may contain an additional reactive site, for example with hydrogel monomers or components to facilitate gelation or to entrap items of interest, such as pharmaceutically or biologically active molecules, agents and entities, as taught herein, or with another structure. Hydrogels of interest can be configured to have a viscosity suitable for the intended use, as known in the art. For example, control of viscosity can be obtained by the monomers and polymers used, using plural initiators, particularly which act by different chemical means, by the level of water trapped in the hydrogel and by incorporated thickeners, such as biopolymers, such as proteins, lipids, saccharides and the like. An example of such a thickener is hyaluronic acid.

The water content of a hydrogel may provide information on the pore structure. Further, the water content may be a factor that influences, for example, the survival of encapsulated cells within the hydrogel. The amount of water that a hydrogel is able to absorb may be related to the cross-linking density and/or pore size. For example, the percentage of methacrylate groups on a functionalized macromer, such as chondroitin sulfate or keratin sulfate, may dictate the amount of water absorbable.

The reagent to form a hydrogel may comprise monomers, macromers, oligomers, polymers, or a mixture thereof. The polymer compositions can consist solely of covalently crosslinkable polymers, or ionically crosslinkable polymers, or polymers crosslinkable by redox chemistry, or polymers crosslinked by hydrogen bonding, or any combination thereof. The polymerizable agent should be substantially hydrophilic and biocompatible.

Suitable hydrophilic polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll™, polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof.

Examples of materials that can be used to form a hydrogel include modified alginates. Alginate is a carbohydrate polymer isolated from seaweed, which can be crosslinked to form a hydrogel by exposure to a divalent cation such as calcium, as described, for example, in WO 94/25080. Alginate is ionically crosslinked in the presence of divalent cations, in water, at room temperature, to form a hydrogel matrix. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemically modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or epsilon-caprolactone. The resulting polymer includes alginate blocks that permit ionically catalyzed gelling, and oligoester blocks that produce more rapid degradation depending on the synthetic design. Alternatively, alginate polymers may be used wherein the ratio of mannuronic acid to glucuronic acid does not produce a film gel, which are derivatized with hydrophobic, water-labile chains, e.g., oligomers of epsilon-caprolactone. The hydrophobic interactions induce gelation, until they degrade in the body.

Alginate is ionically crosslinked in the presence of divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemical modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or ε-caprolactone. The resulting polymer includes alginate blocks that permit ionically catalyzed gelling, and oligoester blocks that produce more rapid degradation depending on the synthetic design. Alternatively, alginate polymers may be used, wherein the ratio of mannuronic acid to glucuronic acid does not produce a firm gel, which are derivatized with hydrophobic, water-labile chains, e.g., oligomers of ε-caprolactone. The hydrophobic interactions induce gelation, until they degrade in the body.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides that gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Polysaccharides that are very viscous liquids or are thixotropic, and form a gel over time by the slow evolution of structure, are also useful. For example, hyaluronic acid, which forms an injectable gel with a consistency like a hair gel, may be utilized. Modified hyaluronic acid derivatives are particularly useful. As used herein, the term "modified hyaluronic acids" refers to chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from Genzyme, Cambridge, Mass. and Fidia, Italy.

Other polymeric hydrogel precursors include polyethylene oxide-polypropylene glycol block copolymers such as Pluronics™ or Tetronics™, which are crosslinked by hydrogen bonding and/or by a temperature change, as described in Steinleitner et al., Obstetrics & Gynecology, 77:48-52 (1991); and Steinleitner et al., Fertility and Sterility, 57:305-308 (1992). Other materials that may be utilized include proteins such as fibrin, collagen and gelatin. Polymer mixtures also may be utilized. For example, a mixture of polyethylene oxide and polyacrylic acid that gels by hydrogen bonding upon mixing may be utilized. In one embodiment, a mixture of a 5% w/w solution of polyacrylic acid with a 5% w/w polyethylene oxide (polyethylene glycol, polyoxyethylene) 100,000 can be combined to form a gel over the course of time, e.g., as quickly as within a few seconds.

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents that can be crosslinked by a radical reaction, for example, on contact with a radical initiator. For example, polymers including ethylenically unsaturated groups that can be photochemically crosslinked may be utilized, as disclosed in WO 93/17669. Hence, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and/or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers, which include cinnamoyl groups that may be photochemically crosslinked, may be utilized, as disclosed in Matsuda et al., ASAID Trans., 38:154-157 (1992).

In general, the polymers are at least partially soluble in aqueous solutions, such as water, buffered salt solutions, or aqueous alcohol solutions. Methods for the synthesis of the other polymers described above are known to those skilled in the art. See, for example Concise Encyclopedia of Polymer Science and Polymeric Amines and Ammonium Salts, E. Goethals, ed. (Pergamon Press, Elmsford, N.Y. 1980). Many polymers, such as poly(acrylic acid), are commercially available. Naturally occurring and synthetic polymers may be modified using chemical reactions available in the art and described, for example, in March, "Advanced Organic Chemistry," 4th Edition, 1992, Wiley-Interscience Publication, New York.

Water soluble polymers with charged side groups may be crosslinked by reacting the polymer with an aqueous solution containing ions of the opposite charge, either cations if the polymer has acidic side groups or anions if the polymer has basic side groups. Examples of cations for crosslinking of the polymers with acidic side groups to form a hydrogel are monovalent cations such as sodium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin.

In the embodiment wherein modified alginates and other anionic polymers that can form hydrogels which are malleable are used to encapsulate cells, the hydrogel is produced by cross-linking the polymer with the appropriate cation, and the strength of the hydrogel bonding increases with either increasing concentrations of cations or of polymer. Concentrations from as low as 0.001 M have been shown to cross-link alginate. Higher concentrations are limited by the toxicity of the salt.

The preferred anions for cross-linking of the polymers to form a hydrogel are monovalent, divalent or trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Suitable ionically crosslinkable groups include phenols, amines, imines, amides, carboxylic acids, sulfonic acids and phosphate groups. Negatively charged groups, such as carboxylate, sulfonate and phosphate ions, can be crosslinked with cations such as calcium ions. The crosslinking of alginate with calcium ions is an example of that type of ionic crosslinking. Positively charged groups, such as ammonium ions, can be crosslinked with negatively charged ions such as carboxylate, sulfonate and phosphate ions. Preferably, the negatively charged ions contain more than one carboxylate, sulfonate or phosphate group.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups. Those polymers can be modified to contain active species polymerizable groups and/or ionically crosslinkable groups. Methods for modifying hydrophilic polymers to include these groups are well known to those of skill in the art.

The polymers and hydrogels may be intrinsically biodegradable, but can be of low biodegradability (for predictability of dissolution) or of sufficiently low molecular weight to allow excretion. The maximum molecular weight to allow excretion in human beings (or other species in which use is intended) will vary with polymer or hydrogel type, but will often be about 20,000 daltons or below. Usable, but less preferable for general use because of intrinsic biodegradability, are water-soluble natural polymers and synthetic equivalents or derivatives, including polypeptides, polynucleotides, and degradable polysaccharides, and hydrogels.

The polymers can be a single block with a molecular weight of at least 600, preferably 2000 or more, and more preferably at least 3000. Alternatively, the polymers can include can be two or more water-soluble blocks which are joined by other groups. Such joining groups can include biodegradable linkages, polymerizable linkages, or both. For example, an unsaturated dicarboxylic acid, such as maleic, fumaric, or aconitic acid, can be esterified with hydrophilic polymers containing hydroxy groups, such as polyethylene glycols, or amidated with hydrophilic polymers containing amine groups, such as poloxamines. For example, see U.S. 2004/0170663.

For example, poly(ethylene oxide)diacrylate (PEODA) may be used in a polymer system for tissue engineering. Cross-linked polymer matrices may include cogels of chondroitin sulfate-methacrylate (CS-MA) and PEODA. The CS-MA hydrogels may absorb more water than the PEODA hydrogels, thus, increasing the percentage of CS-MA in the cogels increases the water content.

The mechanical properties of a cross-linked matrix or interpenetrating network, such as a hydrogel scaffold, may also be related to the hydrogel pore structure. For applications in tissue engineering, scaffolds with different mechanical properties may be desirable depending on the desired clinical application. For example, scaffolds for cartilage tissue engineering in the articular joint must survive higher mechanical stresses than a cartilage tissue engineering system implanted subcutaneously for plastic surgery applications. Thus, hydrogels with mechanical properties that are easily manipulated may be desired.

Examples of suitable polymers include polyethylene glycol (PEG) diacrylate, from a PEG diol; PEG triacrylate, formed from a PEG triol; PEG-cyclodextrin tetraacrylate, formed by grafting PEG to a cyclodextrin central ring, and further acrylating; PEG tetraacrylate, formed by grafting two PEG diols to a bis epoxide and further acrylating; hyaluronic acid methacrylate, formed by acrylating many sites on a hyaluronic acid chain; PEG-hyaluronic acid multiacrylate, formed by grafting PEG to hyaluronic acid and further acrylating; and PEG-unsaturated diacid ester formed by esterifying a PEG diol with an unsaturated diacid.

Photopolymerizable substituents preferably include acrylates, diacrylates, oligoacrylates, dimethacrylates, or oligomethoacrylates, and other biologically acceptable photopolymerizable groups.

The water-soluble macromer may be derived from water-soluble polymers including, but not limited to, poly(ethylene oxide) (PEO), PEG, poly(vinyl alcohol) (PVA), poly(vinylpyrrolidone) (PVP), poly(ethyloxazoline) (PEOX) polyaminoacids, pseudopolyamino acids, and polyethyloxazoline, as well as copolymers of these with each other or other water soluble polymers or water insoluble polymers, provided that the conjugate is water soluble. An example of a water soluble conjugate is a block copolymer of polyethylene glycol and polypropylene oxide, commercially available as a Pluronic™ surfactant.

The hydrogel is made as is known in the art and as provided herein. The hydrogel can be polymerized in situ on the prosthesis surface, for example, or in vitro on the prosthesis, or may be attached on the prosthesis, desiccated and rehydrated just prior to, during or after placement in the body.

A prosthesis or medical device of interest can be used to fill a void or defect in a hard tissue. The coated medical device of interest can be, for example, a disc, affixed in the void or defect using a cement or staple. The coated medical device can substitute for a hard tissue. Thus, a device of interest can substitute for a diseased or damaged hard tissue part. The device then can be attached to a hard surface and may come into contact with the non-calcified, cellular, parenchymal portion of the hard tissue, the marrow. Hence, one surface or end of a device of interest may interface or contact with a marrow cavity of a hard tissue The device can simulate a hard tissue, such as a bone portion or a portion of an articulating joint. Thus a prosthesis of interest can be the ball portion of a ball and socket joint, such as a hip. The shell portion can have a coating of interest on that portion of the shell that interfaces with the acetabulum. The shell also can contain a coating of interest on the concave portion that contacts the ball. Moreover, the shell can have communication means wherein the parenchymal portions of the acetabulum are in contact with one surface of a coated shell of interest and via the communication means are exposed to the portion of the shell that contacts the ball. The ball and stem comprise the other component of the artificial hip. The coated stem is affixed in the parenchymal marrow cavity of the femur. The stem and ball structure can comprise communication means along the length of the stem wherein openings of the communication means can be at the end of the stem distal to the ball, and along the length of the stem, and the other end of the communication means can be found at the surface of the ball. That arrangement connects the marrow with the coating of interest at the surface of the ball Subchondral bone marrow stimulation techniques mobilize blood/bone marrow elements. Once disruption of the vascularized cancellous bone has been performed, a fibrin clot can be formed and serves as a bed for pluripotent cells. Those cells eventually differentiate into "chondrocyte-like" (Allen et al., Sports Med and Arthroscopy Review. 4:51-58, 1996) cells that secrete type I, II and other collagen types inherent to native cartilage content as well as cartilage specific proteoglycans when the proper mechanical and biological cues are provided. The cells produce a fibroblastic repair tissue that on appearance and initial biopsy can have a hyaline-like quality. (Minas & Nehrer, Orthopaedics. 20:525-538, 1997; Ratcliffe & Mow, in Friedlaender & Goldberg (eds.): Bone and Cartilage Allografts. American Academy of Orthopaedic Surgeons, Park Ridge, Ill., 1991, pgs. 123-154).

Microfracture techniques have been developed to enhance chondral resurfacing by providing a suitable environment for new tissue formation and taking advantage of the body's own healing potential. Specially designed awls are used to make multiple perforations, or microfractures, into the subchondral bone plate. Perforations are made as close together as possible, usually approximately 3 to 4 mm apart to avoid the subchondral bone plate fracture. The released marrow elements (including mesenchymal stem cells, growth factors, and other healing proteins) form a surgically induced super clot that provides an enriched environment for new tissue formation. However, the surgeon does not have a control on the release of growth factors into the area. Therefore, the technique relies on body's own healing potential and the rehabilitation program that is crucial to optimize the results of the surgery. It is hoped that ideal physical environment especially the mechanical stimulus (Darling & Athanasiou, Ann Biomed Eng. 2003 October; 31(9):1114-24; Hunter et al., Osteoarthritis Cartilage. 2004 February; 12(2):117-30) for the marrow mesenchymal stem cells to differentiate into articular cartilage-like cells is promoted, which is ultimately leading to development of a durable repair cartilage that fills the original defect (Steadman et al., Clin Orthop. 2001 October; (391 Suppl):S362-9).

Subchondral drilling consists of drilling through the defect to penetrate the subchondral bone. The technique was first popularized in the late 1950's by Pridie, (Pridie, J Bone Joint Surg Br. 41B:618, 1959) and subsequent findings suggest the repair tissue introduced into the area can look like grossly like hyaline cartilage but histologically resembles fibrocartilage (Shapiro et al., J Bone Joint Surg. 75A:532-553, 1993).

Microfracture is another such technique in which the lesion is exposed, debrided, and a series of small fractures about 3 to 4 mm in depth are produced with an awl. Adjacent cartilage is debrided to a stable cartilaginous rim, and any loose fragments and fibrous tissue are removed. Microfracture has a few advantages over drilling: no heat necrosis, the awl creates more exposed surface area for clot formation, and the structural integrity of the subchondral bone is maintained. Although that method has been widely used in orthopedics, the formation of fibrocartilage could not be prevented.

Stimulating articular cartilage growth through the use of various grafting techniques has recently been reported. Utilizing autologous tissue or allografts, these procedures are designed to provide a suitable environment for stimulation of the mesenchymal cells to produce type II collagen fibers. The success of such approaches is at least partly related to the severity of the abnormalities, graft and technique utilized, age of the patient, joints involved, correction of associated pathology, weight bearing restrictions and the use of postoperative continuous passive motion. Wirth & Rudert, Arthroscopy: The Journal of Arthroscopic and Related Surgery. 12:300-308, 1996). Intact full thickness grafts suffer the problems of mismatched sizes, immunologic rejection, and tissue structural weakening during the process of revascularization.

The above methods serve to mobilize elements from the marrow cavity as well as enable access to the marrow contents. Those methods may be practiced prior to placement of a coated prosthesis or implantable device of interest. The adhesive and hydrogel of interest serve as a site of attachment or as a conduit for marrow elements as well as enable nutrient movement to and from the marrow to portions on the device of interest remote from the cell or nutrient source While allogeneic and xenogeneic cells can be used, compatibility is maximal when autologous cells and tissues are used. Accordingly, by enabling the movement of cells and the like through a device of interest, those migratory cells can establish new sites of tissue and organ development Thus, in the context of a bone prosthesis, said prosthesis can contain communication means between the marrow contents in the core of the bone and the external surface of the prosthesis. The communication means can be manufactured conduits or tubes, for example, or may arise from the use of a mesh or other porous material to construct the prosthesis. The communication means enables cells from the marrow to relocate to a site proximal to the external surface of the prosthesis or at the surface of the prosthesis, wherein said cells can differentiate into cells, such as chondrocytes. As noted herein, the adhesives and hydrogels of interest can be loaded with various biologically active agents, such as those which may serve a nutrient and differentiating function for such marrow cells.

A polymer of interest, a device of interest, a coated device of interest, a hydrogel of interest can be presented in the form of a kit. The reagents and products of interest are provided in a format as known in the art, for example, monomers of a hydrogel can be present in dry form in a vial, a polymer of interest can be provided as a liquid for application, again in a vial, a coated device can be presented in a dry or wet state in a sealed package ready for use, and so on.

To prolong shelf life and to comply with regulatory guidelines for use with animals and humans, the reagents and components for practicing the invention, and for inclusion in a kit, can be sterilized. Chemical reagents can be exposed to forms of sterilization suitable to the reagent as known in the art. Thus, some chemical reagents can be heat sterilized, for example, using steam, or pasteurized. Other reagents can be sterilized by passage through filtration media that can remove pathogens, such as a membrane filter of appropriate pore size. Alternatively, cold sterilization techniques can be practiced to avoid using heat. Suitable cold sterilization techniques include use of ethylene oxide, irradiation, using gamma rays, x-rays, electron beams, plasma or microwaves, ozone and the like. Some of the cold sterilization techniques may be performed below ambient temperature including below 0 degrees C. The sterilization can be performed at ambient, lower or higher pressures. Also, ambient or inert atmosphere can be used. Additionally, excipients, such as sugars, organic acids, such as ascorbate or citric acid, and other stabilizers can be added to the reagents prior to sterilization.

It should be understood that various changes and modifications to the presently preferred embodiments described herein will be apparent to those skilled in the art. Such changes and modifications can be made without departing from the spirit and scope of the present invention and without diminishing its intended advantages.

All references cited herein, are herein incorporated by reference in entirety.

The invention is claimed as follows:

1. A medical device for implantation to bone or cartilage, comprising (a) a biocompatible implantable material selected from the group consisting of metal, plastic, ceramics and combinations thereof, and, attached to a surface thereof, (b) a biocompatible polymer adhesive comprising a polysaccharide having at least two functional groups, including a first functional group comprising an acrylate or methacrylate moiety and a second functional group comprising an aldehyde moiety, and (c) at least one coating comprising a structure or biologically active agent attached to said polymer adhesive.

2. The medical device of claim 1, wherein said implantable material comprises a metal.

3. The medical device of claim 2, wherein said surface is textured.

4. The medical device of claim 3, wherein said textured surface comprises pores or pits.

5. The medical device of claim 1, wherein said implantable material comprises a plastic.

6. The medical device of claim 1, wherein said implantable material comprises a ceramic.

7. The medical device of claim 1, wherein said polysaccharide is keratan sulfate, hyaluronate or chondroitin sulfate.

8. The medical device of claim 1, wherein said at least one coating comprises a cell.

9. The medical device of claim 1, wherein said biologically active agent is a factor inducing bone or cartilage development.

10. The medical device of claim 1, further comprising a second biocompatible polymer comprising at least two functional groups, wherein said second polymer is attached to said at least one coating.

11. The medical device of claim 1, wherein said polymer adhesive is bonded to said implantable material through said first functional group.

12. The medical device of claim 11, wherein coating is bonded to said polymer adhesive through said second functional group.

13. A medical device for implantation in contact with tissue, said device having a surface comprising (i) a biocompatible material selected from the group consisting of metal, plastic, ceramics and combinations thereof, and (ii) a functionalized polysaccharide polymer adhered to said surface, wherein the functionalized polysaccharide polymer comprises (a) a first functional moiety comprising a methacrylate or methacrylate group bonded to said surface, and (b) a second functional moiety comprising aldehyde reactive sites for bonding with other compounds.

14. The medical device according to claim 13, wherein the biocompatible material is selected from the group consisting of metals, ceramics, polymers, and composites and mixtures thereof.

15. The medical device according to claim 14, wherein the biocompatible material is a polymer reactive with said first reactive moiety of said functionalized polysaccharide polymer.

16. The medical device according to claim 13, wherein said tissue is reactive with said aldehyde reactive sites.

17. The medical device according to claim 16, wherein said tissue is bone tissue.

18. The medical device according to claim 17, wherein the device can be used to fill a void or defect in hard tissue or substitute for hard tissue.

19. The medical device according to claim 18, wherein the device is a replacement joint or a replacement bone or bone part.

20. The medical device according to claim 13, wherein said functionalized polysaccharide polymer comprises chondroitin.

21. The medical device according to claim 20, wherein the biocompatible material is a polymer reactive with said first reactive moiety of said functionalized polysaccharide polymer; and wherein said tissue is reactive with said aldehyde reactive sites.

22. A medical device for implantation in contact with tissue, said device having a surface comprising (a) a biocompatible implantable material, (b) a functionalized chondroitin sulfate adhesive, bonded to said material, having a first functional group comprising an acrylate or methacrylate moiety and a second functional group comprising an aldehyde moiety, and (c) a coating, bonded to said adhesive, comprising a biologically active agent.

23. The medical device according to claim 22, wherein the biocompatible material is selected from the group consisting of metals, ceramics, polymers, and composites and mixtures thereof.

24. The medical device according to claim 22, wherein said biologically active agent is selected from the group consisting of enzymes, hormones, growth factors, antimicrobial agents, cells and combinations thereof.

25. A medical device, for implantation in bone, comprising
(a) a first prosthesis having a surface,
(b) a second prosthesis having a surface; and
(c) a functionalized chondroitin polymer adhesive comprising (i) a first functional moiety comprising a methacrylate or methacrylate group bonded to the surface of said first prosthesis, and (ii) a second functional moiety comprising aldehyde reactive sites bonded to the surface of said second prosthesis.

26. The medical device according to claim 25, wherein the first and second prosthesis each comprise a biocompatible material independently selected from the group consisting of metals, ceramics, plastics, and composites and mixtures thereof.

* * * * *